United States Patent

Yahiaoui et al.

[11] Patent Number: 6,060,636
[45] Date of Patent: May 9, 2000

[54] TREATMENT OF MATERIALS TO IMPROVE HANDLING OF VISCOELASTIC FLUIDS

[75] Inventors: Ali Yahiaoui, Roswell; Jack Nelson Lindon; Arthur Edward Garavaglia, both of Alpharetta; Crystal Sutphin Leach, Atlanta; Connie Lynn Hetzler, Alpharetta, all of Ga.; Garry Roland Woltman, Neenah, Wis.; David Charles Potts, Dunwoody, Ga.

[73] Assignee: Kimberly-Clark Worldwide, Inc., Neenah, Wis.

[21] Appl. No.: 08/905,264

[22] Filed: Aug. 1, 1997

Related U.S. Application Data

[60] Provisional application No. 60/025,609, Sep. 4, 1996.

[51] Int. Cl.[7] ..................................................... A61F 13/15
[52] U.S. Cl. .......................... 604/367; 604/358; 604/375; 604/385.1; 604/365
[58] Field of Search ................................. 71/8; 424/443; 604/370, 380, 367, 358, 375, 385.1, 365; 128/285; 510/433, 421; 526/240

[56] References Cited

U.S. PATENT DOCUMENTS

| | | | |
|---|---|---|---|
| 2,474,885 | 7/1949 | Blomquist | 18/8 |
| 2,712,489 | 7/1955 | Abbott, Jr. | 18/54 |
| 3,238,563 | 3/1966 | Hoffman | 18/12 |

(List continued on next page.)

FOREIGN PATENT DOCUMENTS

| | | | |
|---|---|---|---|
| 0 009 977 | 4/1980 | European Pat. Off. | A61L 15/00 |
| 0 053 221 | 6/1982 | European Pat. Off. | A61L 15/00 |
| 0 093 358 | 11/1983 | European Pat. Off. | |
| 0 586 205 | 3/1994 | European Pat. Off. | B29C 47/16 |
| 249 288 | 9/1987 | Germany | D01D 5/08 |
| 475278 | 6/1975 | Russian Federation | 264/176.1 |
| 1 068 667 | 5/1967 | United Kingdom . | |
| 87/03208 | 6/1987 | WIPO | A61L 15/00 |
| 94/22501 | 10/1994 | WIPO | A61L 15/46 |

OTHER PUBLICATIONS

*Polymer Blends & Composites* (p. 7) by John A. Manson and Leslie H. Sperling, copyright 1976 by Plenum Press, a div. of Plenum Publishing Corp. of New York, IBSN 03–306–30831–2, pp. 273–277.

"Fabrication of a Continuous Wettability Gradient by Radio Frequency Plasma Discharge," W. G. Pitt, *J. Colloid Interface Sci.*, 133, No. 1, 223 (1989).

"Wettability Gradient Surfaces Prepared by Corona Discharge Treatment," J. H. Lee, et al., *Transaction of the 17th Annual Meeting of the Society for Biomaterials*, May 1–5, 1991, p. 133, Scottsdale, Arizona.

Coassigned Provisional Patent Application S.N. 60/046,702 filed May 14, 1997 entitled, "Artificial Bodily Fluid".

Coassigned U.S. application No. 08/665,172, 172 to Yahiaoui, Ning, Bolian, McDowall, Potts and Van Hout filed Jun. 14, 1996, Docket No. 12092.

ICI Americas Inc. Technical Bulletin "Ahcovel Base N–62 Liquid Nonionic Textile Softener", 1978.

*Primary Examiner*—John G. Weiss
*Assistant Examiner*—Miley Craig Peppers, III
*Attorney, Agent, or Firm*—William D. Herrick

[57] ABSTRACT

Disclosed is an improved structure that includes a nonwoven web including a viscoelastant treatment. The treated web, when contacted by a viscoelastic fluid such as menses alters the viscoelastic properties of the fluid and enhances its wicking and distribution throughout the absorbent structure. A desirable viscoelastant is a alkyl polyglycoside, particularly those having 8 to 10 carbon atoms in the alkyl chain. When applied so as to provide an amount of about 0.1% to about 5.0% solids add-on based on the weight of the dry nonwoven web, rapid fluid wicking and distribution may be obtained. Other viscoelastants are disclosed. Advantageously the treatment may be applied as a high solids composition using conventional application means such as spray coaters and the like or as an internal additive. The absorbent structure finds particular utility as a distribution layer component of a sanitary napkin for absorbing menses as well as other blood handling products such as surgical drapes, for example.

23 Claims, 6 Drawing Sheets

U.S. PATENT DOCUMENTS

| | | | |
|---|---|---|---|
| 3,239,881 | 3/1966 | Larsen | 18/12 |
| 3,293,689 | 12/1966 | Chiselko et al. | 18/12 |
| 3,309,436 | 3/1967 | Larsen | 264/25 |
| 3,320,634 | 5/1967 | Ryan et al. | 18/12 |
| 3,338,992 | 8/1967 | Kinney | 264/24 |
| 3,341,394 | 9/1967 | Kinney | 161/72 |
| 3,502,538 | 3/1970 | Petersen | 161/150 |
| 3,502,763 | 3/1970 | Hartmann | 264/210 |
| 3,542,615 | 11/1970 | Dobo et al. | 156/181 |
| 3,598,865 | 8/1971 | Lew | 260/210 |
| 3,621,526 | 11/1971 | Bell, Jr. et al. | 18/8 P |
| 3,647,346 | 3/1972 | Minnie | 425/466 |
| 3,692,618 | 9/1972 | Dorschner et al. | 161/72 |
| 3,706,518 | 12/1972 | Bunte et al. | 425/381 |
| 3,802,817 | 4/1974 | Matsuki et al. | 425/66 |
| 3,829,274 | 8/1974 | Melead | 425/466 |
| 3,849,241 | 11/1974 | Butin et al. | 161/169 |
| 3,855,046 | 12/1974 | Hansen et al. | 161/150 |
| 3,913,421 | 10/1975 | Hawkins | 76/107 S |
| 3,947,214 | 3/1976 | Cunningham | 425/467 |
| 3,951,945 | 4/1976 | Heesen et al. | 260/210 |
| 3,966,918 | 6/1976 | Kawamata et al. | 424/182 |
| 3,984,508 | 10/1976 | Solop | 264/40.1 |
| 4,041,203 | 8/1977 | Brock et al. | 428/157 |
| 4,057,385 | 11/1977 | Yazaki et al. | 425/466 |
| 4,098,564 | 7/1978 | Michalski | 425/461 |
| 4,204,821 | 5/1980 | Gauchel et al. | 425/131.1 |
| 4,248,579 | 2/1981 | Maejima | 425/227 |
| 4,330,254 | 5/1982 | Cunningham | 425/466 |
| 4,340,563 | 7/1982 | Appel et al. | 264/518 |
| 4,374,888 | 2/1983 | Bornslaeger | 428/198 |
| 4,381,184 | 4/1983 | Hurni et al. | 425/202 |
| 4,422,839 | 12/1983 | Przytulla et al. | 425/465 |
| 4,432,718 | 2/1984 | Wurzer | 425/466 |
| 4,460,644 | 7/1984 | Pavlich | 428/314.4 |
| 4,479,768 | 10/1984 | Kube et al. | 425/192 R |
| 4,488,928 | 12/1984 | Khan et al. | 156/495 |
| 4,552,712 | 11/1985 | Ramamurthy | 264/85 |
| 4,627,931 | 12/1986 | Malik | 252/153 |
| 4,659,302 | 4/1987 | Maejima | 425/190 |
| 4,753,844 | 6/1988 | Jones et al. | 428/288 |
| 4,764,505 | 8/1988 | Fujinuma et al. | 514/35 |
| 4,789,588 | 12/1988 | Suzuki et al. | 428/288 |
| 4,871,493 | 10/1989 | Goto | 264/40.6 |
| 4,875,846 | 10/1989 | Reinbold | 425/186 |
| 4,895,622 | 1/1990 | Barnett et al. | 162/199 |
| 4,914,170 | 4/1990 | Chang et al. | 526/240 |
| 4,995,884 | 2/1991 | Ross et al. | 8/115.6 |
| 5,045,387 | 9/1991 | Schmalz | 428/284 |
| 5,057,361 | 10/1991 | Sayovitz et al. | 428/290 |
| 5,074,854 | 12/1991 | Davis | 604/385.1 |
| 5,108,820 | 4/1992 | Kaneko et al. | 428/198 |
| 5,108,827 | 4/1992 | Gessner | 428/219 |
| 5,109,127 | 4/1992 | Sekiguchi et al. | 536/115 |
| 5,145,689 | 9/1992 | Allen et al. | 425/72.2 |
| 5,147,197 | 9/1992 | Hodan et al. | 425/192 S |
| 5,154,855 | 10/1992 | Sekiguchi et al. | 252/312 |
| 5,169,706 | 12/1992 | Collier, IV et al. | 428/152 |
| 5,190,747 | 3/1993 | Sekiguchi et al. | 424/56 |
| 5,208,047 | 5/1993 | Cloeren et al. | 425/141 |
| 5,238,385 | 8/1993 | Johnson | 425/183 |
| 5,238,586 | 8/1993 | Uphues et al. | 252/8.6 |
| 5,268,132 | 12/1993 | Keilert et al. | 264/169 |
| 5,273,704 | 12/1993 | Scholl et al. | 264/252 |
| 5,292,463 | 3/1994 | Paul | 264/40.6 |
| 5,310,730 | 5/1994 | Fujinuma et al. | 514/35 |
| 5,336,552 | 8/1994 | Strack et al. | 428/224 |
| 5,342,534 | 8/1994 | Skrobala et al. | 252/91 |
| 5,362,497 | 11/1994 | Yamada et al. | 424/449 |
| 5,373,044 | 12/1994 | Adams et al. | 524/379 |
| 5,382,400 | 1/1995 | Pike et al. | 264/168 |
| 5,397,227 | 3/1995 | Hodan et al. | 425/192 S |
| 5,401,454 | 3/1995 | Mendel | 264/176.1 |
| 5,421,941 | 6/1995 | Allen et al. | 156/244.11 |
| 5,424,018 | 6/1995 | Paul et al. | 264/176.1 |
| 5,451,357 | 9/1995 | Cloeren | 264/173.16 |
| 5,456,869 | 10/1995 | Miles et al. | 264/39 |
| 5,468,797 | 11/1995 | Adams et al. | 524/379 |
| 5,474,776 | 12/1995 | Koyanagi et al. | 424/401 |
| 5,501,813 | 3/1996 | Fischer et al. | 252/174.17 |
| 5,503,076 | 4/1996 | Yeo | 101/483 |
| 5,505,609 | 4/1996 | Cloeren et al. | 425/381 |
| 5,507,498 | 4/1996 | Trott | 277/1 |
| 5,540,979 | 7/1996 | Yahiaoui et al. | 428/212 |
| 5,550,189 | 8/1996 | Qin et al. | 525/54.3 |
| 5,567,808 | 10/1996 | Desai et al. | 536/4.1 |
| 5,605,683 | 2/1997 | Desai et al. | 424/70.11 |
| 5,669,798 | 9/1997 | Koczab | 442/362 |
| 5,700,772 | 12/1997 | Isobe et al. | 510/421 |
| 5,733,822 | 3/1998 | Gessner et al. | 442/35 |
| 5,744,441 | 4/1998 | Urfer et al. | 510/433 |
| 5,759,569 | 6/1998 | Hird et al. | 424/443 |

TREATMENT OF MATERIALS TO IMPROVE HANDLING OF VISCOELASTIC FLUIDS

This application claims priority from U.S. Provisional Application No. 60/025,609 filed Sep. 4, 1996.

BACKGROUND

There are numerous applications for materials that can rapidly absorb and/or transfer fluids such as bodily wastes and the like. Examples include disposable personal care products such as disposable diapers and training pants, feminine hygiene products such as sanitary napkins and tampons, and incontinent care products such as pads and undergarments. Other industrial products such as wipers, oilsorb products and soakers have such requirements as do health care items such as bandages, for example. Because these fluids have different properties, it is difficult to provide a material adapted to fill many of these needs with an economy consistent with disposability that many such applications require. In particular, fluids such as menses, for example, have viscoelastic properties that challenge traditional absorption and distribution concepts. The viscosity and/or elastic components of such fluids tend to impose unique requirements for absorption and/or distribution. These requirements are often inconsistent with the best performance with respect to other components of the fluid that are less viscous or elastic with the result that a compromise in overall performance usually is required. For example, the pore and capillary sizes in an ideal material for absorbing and distributing less viscoelastic components are different from those that work best for the more viscoelastic components. Much effort has been expended to develop a material structure in nonwovens, foams, films and the like that meets all of these needs, but without complete success. Another approach is to modify the viscoelastic properties of the fluid itself. Numerous approaches have been employed to modify the bulk properties of viscoelastic fluids, including agents which affect intermolecular bonding and the physical entanglements of macromolecules.

Nonwoven fabrics and their manufacture have been the subject of extensive development resulting in a wide variety of materials for numerous applications. For example, nonwovens of light basis weight and open structure are used in personal care items such as disposable diapers as liner fabrics that provide dry skin contact but readily transmit fluids to more absorbent materials which may also be nonwovens of a different composition and/or structure. For many applications the ability to wick or transport viscous fluids such as menses is important for effective performance of these products by distributing the fluid to provide maximum use of absorbent properties of that or underlying materials. For other applications, nonwovens of heavier weights may be designed with pore structures making them suitable for filtration, absorbent and barrier applications such as wrappers for items to be sterilized, wipers or protective garments for medical, veterinary or industrial uses. Even heavier weight nonwovens have been developed for recreational, agricultural and construction uses. These are but a few of the practically limitless examples of types of nonwovens and their uses that will be known to those skilled in the art who will also recognize that new nonwovens and uses are constantly being identified. There have also been developed different ways and equipment to make nonwovens having desired structures and compositions suitable for these uses. Examples of such processes include spunbonding, meltblowing, carding, and others which will be described in greater detail below. The present invention has general applicability to nonwovens as will be apparent to one skilled in the art, and it is not to be limited by reference or examples relating to specific nonwovens which are merely illustrative.

It is not always possible to efficiently produce a nonwoven having all the desired properties as formed, and it is frequently necessary to treat the nonwoven to improve or alter properties such as wettability by one or more fluids, wicking or distribution properties, repellency to one or more fluids, electrostatic characteristics, conductivity, and softness, to name just a few examples. Conventional treatments involve steps such as dipping the nonwoven in a treatment bath, coating or spraying the nonwoven with the treatment composition, and printing the nonwoven with the treatment composition. For cost and other reasons it is usually desired to use the minimum amount of treatment composition that will produce the desired effect with an acceptable degree of uniformity. It is known, for example, that the heat of an additional drying step to remove water applied with the treatment composition can deleteriously affect strength properties of the nonwoven as well as add cost to the process. It is, therefore, desired to provide an improved treatment process and/or composition for nonwovens that can efficiently and effectively apply the desired treatment without adversely affecting desirable nonwoven web properties while also achieving the desired results. More particularly, it is desired to provide a treated nonwoven adapted for use with viscoelastic fluids and having the property of altering the characteristics such as viscosity and/or elasticity of a viscoelastic insult liquid so as to control fluid movement such as intake, distribution, and absorption, of the liquid in personal care product applications such as sanitary napkins.

SUMMARY OF THE INVENTION

The present invention is directed to structures particularly adapted to receive fluids having viscoelastic properties such as menses, mucous, blood products, feces, and others which will be apparent to those skilled in the art. The structures of the invention are useful as feminine hygiene products such as menses absorbing devices like sanitary napkins and tampons, infant and child care products such as disposable diapers and training pants, bandages, incontinent products, and products for wiping and absorbing oils, for example. In accordance with the invention the structure comprises a synthetic, often normally hydrophobic, substrate containing a viscoelastant agent placed so as to contact the viscoelastic fluid. Advantageously the substrate is a nonwoven and may be, for example, a spunbond, meltblown, coformed or bonded carded web. Additional substrates which can be used include foams and films that are fibrillated, apertured or otherwise treated to have fiber-like properties as well as laminates of these and/or nonwovens. Depending on the particular application, the structure may be used as a body contact liner, a distribution layer between a liner and an absorbent layer, an absorbent layer, or in more than one of these layers. On contact the structure of the invention alters the viscoelastic properties of the fluid so as to improve fluid intake, distribution and absorption properties. Desirably the viscoelastant agent is one that is harmless in use and environmentally friendly upon disposal. Useful examples include alkyl polyglycosides having 8–10 carbon atoms in the alkyl chain.

These alky polyglycosides alter the viscoelastic properties of viscoelastic fluids as well as increase the wettability of synthetic surfaces. Other examples of viscoelastants include bovine lipid extract surfactant (Survanta, Ross Laboratories), a drug used to treat Acute Respiratory Distress Syndrome and Cystic Fibrosis, and enzymes such as papain or pepsin which cleave protein structures. Some dextrins and dextrans may also be used as viscoelastants. Dextrans (macrose) are polymers of glucose with chain-like structures and molecular weights up to, for example, 200,000 produced from sucrose, often by bacterial action. As is known, dextrins (starch gum) are normally solid starch derivatives formed often when starch is heated either alone or with nitric acid for example, 4000 MW dextran from Polydex Pharmaceuticals, Ltd. Of Scarborough, Canada. The normally hydrophobic substrate may be additionally or simultaneously treated for increased wettability by a surfactant if desired. The addition of the viscoelastant agent to the substrate may be accomplished by conventional means such as spraying, coating, dipping and the like although the use of high solids spray is advantageous in cases where drying and/or compression is desired to be minimized. Alternatively, in some cases it may be advantageous to add the viscoelastant as an internal additive to the polymer melt. The amount of the viscoelastant agent used will depend on the particular end use as well as factors such as basis weight and porosity of the substrate.

TEST METHODS

Figure 1:
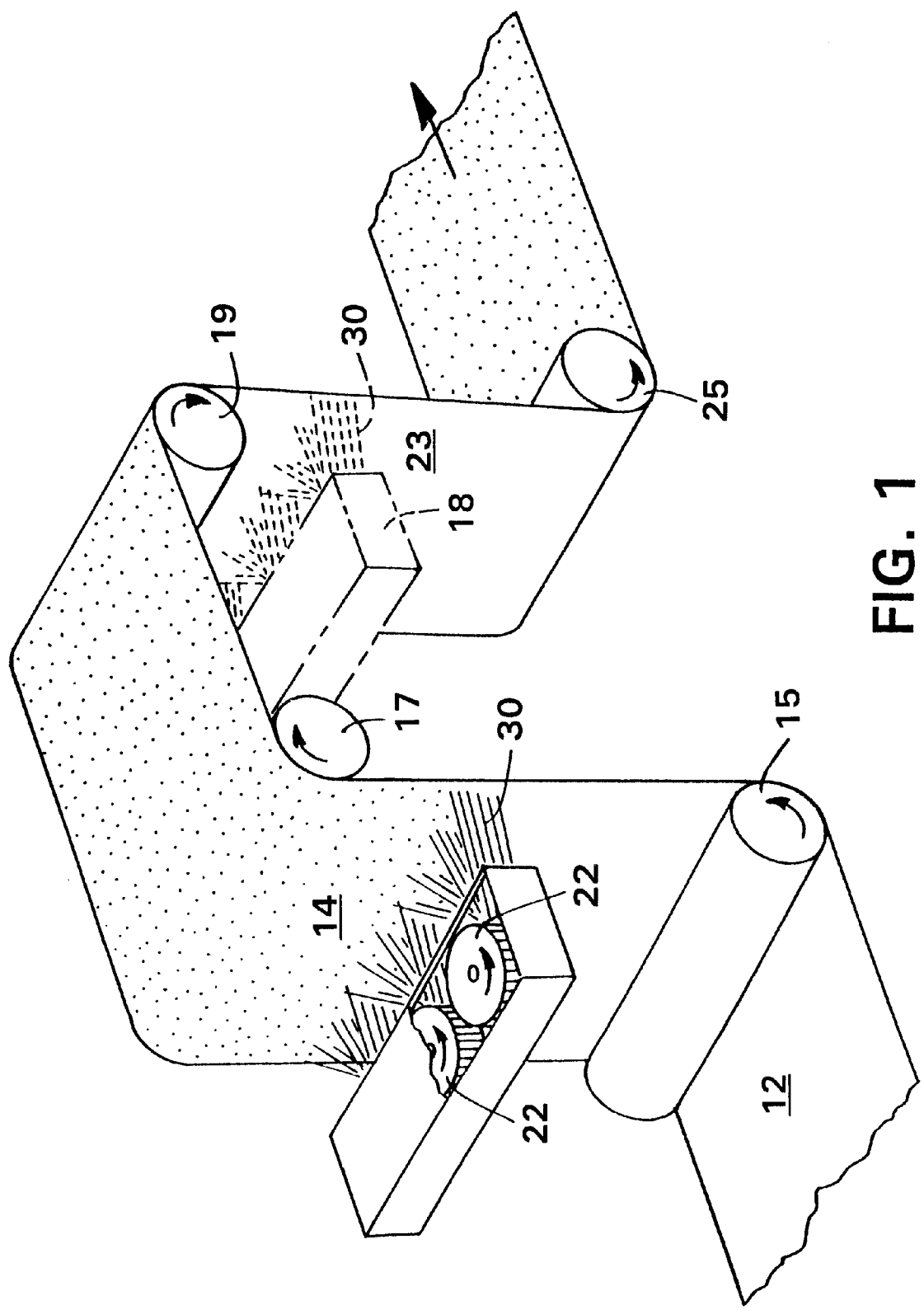
FIG. 1 is a schematic illustration of a treating process of the present invention useful for application to one or both sides of the nonwoven web.

The viscoelastic properties were determined by a procedure specified in the Operations Manual for the VILASTIC 3 Viscoelastic Analyzer (VILASTIC SCIENTIFIC, INC., P.O. Box 160261, Austin, Tex. 78716 USA). The instrument was calibrated by the manufacturer and the calibration was checked prior to sample measurements. The coupling fluid used was Immunosaline (VWR Scientific). The measurements were made in the "Stretchr" mode at a frequency of 0.05 Hz, with an integration time of 39 seconds, at ambient conditions, at the medium drive setting, and with a medium size sample tube (stainless steel, inside radius of 0.0916 cm, and length of 6.561 cm).

Wicking results were determined by a method described in U.S. Pat. No. 5,314,582 to Nguyen and Vargas. Wicking was performed in a horizontal mode, at ambient conditions, with no weight used to confine samples. One-by-eight inch samples (eight inches in machine direction) were used, with a sample size of five. Results are reported as the distance wicked (inches) in twenty minutes.

The following test procedure was utilized to evaluate the intake capability of feminine care pads. A Harvard Apparatus Syringe Pump was used to deliver 250 µL drops of menses simulant from a 30-cc syringe at a rate of 3 ml/min. The fluid was delivered through 1/16 in. (I.D.) tubing attached to the syringe. A Plexiglas plate was used to control placement of the end of the tubing just slightly above the top surface of the test material. The pump was set to deliver a drop, then pause for thirty seconds before delivery of the next drop. A stopwatch was used to record the time taken for the drop to totally penetrate through the top layer into the product. A total of three drops (750 µl) were delivered to a single test spot on a product. The product was then repositioned and a second test spot was insulted in the same manner. Five replicates of each test code were evaluated.

The viscoelastic fluid used in the rheological and wicking studies was either homogenized chicken eggwhite prepared by drawing and expelling 50 cc of eggwhite into and out of a 60 cc disposable syringe at a flow rate of 100 cc/minute, and repeating the process for a total of five cycles (Fluid A) or synthetic menses simulant as described in coassigned U.S. Pat. No. 5,883,231 filed as provisional patent application Ser. No. 60/046,702 filed May 14, 1997 entitled "Artificial Bodily Fluid," the contents of which are incorporated herein by reference in its entirety (Fluid B). Fluid B contained a fluid designed to simulate the viscoelastic and other properties of menses. In order to prepare the fluid, blood, in this case defibrinated swine blood, was separated by centrifugation at 3000 rpm for 30 minutes, though other methods or speeds and times may be used if effective. The plasma was separated and stored separately, the buffy coat removed and discarded and the packed red blood cells stored separately as well. Eggs, in this case jumbo chicken eggs, were separated, the yolk and chalazae discarded and the egg white retained. The egg white was separated into thick and thin portions by straining the white through a 1000 micron nylon mesh for about 3 minutes, and the thinner portion discarded. Note that alternative mesh sizes may be used and the time or method may be varied provided the viscosity is at least that required. The thick portion of egg white which was retained on the mesh was collected and drawn into a 60 cc syringe which was then placed on a programmable syringe pump and homogenized by expelling and refilling the contents five times. In this example, the amount of homogenization was controlled by the syringe pump rate of about 100 ml/min, and the tubing inside diameter of about 0.12 inches. After homogenizing the thick egg white had a viscosity of about 20 centipoise at 150 $sec^{-1}$ and it was then placed in the centrifuge and spun to remove debris and air bubbles at about 3000 rpm for about 10 minutes, though any effective method to remove debris and bubbles may be used.

After centrifuging, the thick, homogenized egg white, which contains ovomucin, was added to a 300 cc Fenwal® Transfer pack using a syringe. Then 60 cc of the swine plasma was added to the transfer pack. The transfer pack was clamped, all air bubbles removed, and placed in a Stomacher lab blender where it was blended at normal (or medium) speed for about 2 minutes. The transfer pack was then removed from the blender, 60 cc of swine red blood cells were added, and the contents mixed by hand kneading for about 2 minutes or until the contents appeared homogenous. A hematocrit of the final mixture showed a red blood cell content of about 30 weight percent and generally should be at least within a range of 28–32 weight percent for artificial menses made according to this example. The amount of egg white was about 40 weight percent.

The ingredients and equipment used in the preparation of this artificial menses are readily available. Below is a listing of sources for the items used in the example, though of course other sources may be used providing they are approximately equivalent.

Blood (swine): Cocalico Biologicals, Inc., 449 Stevens Rd., Reamstown, Pa. 17567, (717) 336-1990.

Fenwal® Transfer pack container, 300 ml, with coupler, code 4R2014: Baxter Healthcare Corporation, Fenwal Division, Deerfield, Ill. 60015.

Harvard Apparatus Programmable Syringe Pump model no. 55-4143: Harvard Apparatus, South Natick, Mass. 01760.

Stomacher 400 laboratory blender model no. BA 7021, serial no. 31968: Seward Medical, London, England, UK.

1000 micron mesh, item no. CMN-1000-B: Small Parts, Inc., PO Box 4650, Miami Lakes, Fla. 33014-0650.

Hemata Stat-II device to measure hemocrits, serial no. 1194Z03127: Separation Technology, Inc., 1096 Rainer Drive, Altamont Springs, Fla. 32714.

DETAILED DESCRIPTION OF THE INVENTION

DEFINITIONS

As used herein the term "viscoelastic" means a composition having at least one significant component that is moderately viscous and/or has elastic properties. By "moderately viscous" it is meant that the component has a viscosity of at least that of normal human blood plasma. By "elastic" it is meant that the component has elasticity equal to or greater than normal human blood plasma.

As used herein, the term "viscoelastant" means an organic agent that, when an effective amount is contacted by a viscoelastic composition, materially alters the properties of that viscoelastic composition, for example, by reducing its viscosity and/or elastic nature. By "materially alters" it is meant that the property measured as described is changed by at least a statistically significant amount and, advantageously, this change will be at least about 30% for many applications.

As used herein the term "nonwoven fabric or web" means a web having a structure of individual fibers or threads which are interlaid, but not in a regular or identifiable manner as in a knitted fabric. The term also includes individual filaments and strands, yarns or tows as well as foams and films that have been fibrillated, apertured, or otherwise treated to impart fabric-like properties. Nonwoven fabrics or webs have been formed from many processes such as for example, meltblowing processes, spunbonding processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

As used herein the term "microfibers" means small diameter fibers having an average diameter not greater than about 75 microns, for example, having an average diameter of from about 0.5 microns to about 50 microns, or more particularly, microfibers may have an average diameter of from about 2 microns to about 40 microns. Another frequently used expression of fiber diameter is denier, which is defined as grams per 9000 meters of a fiber and may be calculated as fiber diameter in microns squared, multiplied by the density in grams/cc, multiplied by 0.00707. A lower denier indicates a finer fiber and a higher denier indicates a thicker or heavier fiber. For example, the diameter of a polypropylene fiber given as 15 microns may be converted to denier by squaring, multiplying the result by 0.89 g/cc and multiplying by 0.00707. Thus, a 15 micron polypropylene fiber has a denier of about 1.42 ($15^2 \times 0.89 \times 0.00707 = 1.415$). Outside the United States the unit of measurement is more commonly the "tex", which is defined as the grams per kilometer of fiber. Tex may be calculated as denier/9.

As used herein the term "spunbonded fibers" refers to small diameter fibers which are formed by extruding molten thermoplastic material as filaments from a plurality of fine, usually circular capillaries of a spinneret with the diameter of the extruded filaments then being rapidly reduced as, for example, described in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Levy, and U.S. Pat. No. 3,542,615 to Dobo et al. Spunbond fibers are quenched and generally not tacky when they are deposited onto a collecting surface. Spunbond fibers are generally continuous and have average diameters frequently larger than 7 microns, more particularly, between about 10 and 20 microns.

As used herein the term "meltblown fibers" means fibers formed by extruding a molten thermoplastic material through a plurality of fine, usually circular, die capillaries as molten threads or filaments into converging high velocity, usually heated, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface often while still tacky to form a web of randomly dispersed meltblown fibers. Such a process is disclosed, for example, in U.S. Pat. No. 3,849,241 to Butin. Meltblown fibers are microfibers which may be continuous or discontinuous and are generally smaller than 10 microns in average diameter.

As used herein "bonded carded webs" or "BCW" refers to nonwoven webs formed by carding processes as are known to those skilled in the art and further described, for example, in coassigned U.S. Pat. No. 4,488,928 to Alikhan and Schmidt which is incorporated herein in its entirety by reference. Briefly, carding processes involve starting with a blend of, for example, staple fibers with bonding fibers or other bonding components in a bulky batt that is combed or otherwise treated to provide a generally uniform basis weight. This web is heated or otherwise treated to activate the adhesive component resulting in an integrated, usually lofty nonwoven material.

As used herein the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configuration of the material. These configurations include, but are not limited to isotactic, syndiotactic and random symmetries.

As used herein the term "monocomponent" fiber refers to a fiber formed from one or more extruders using only one polymer. This is not meant to exclude fibers formed from one polymer to which small amounts of additives have been added for color, anti-static properties, lubrication, hydrophilicity, etc. These additives, e.g. titanium dioxide for color, are generally present in an amount less than 5 weight percent and more typically about 2 weight percent.

As used herein the term "conjugate fibers" refers to fibers which have been formed from at least two polymers extruded from separate extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such a conjugate fiber may be, for example, a sheath/core arrangement wherein one polymer is surrounded by another or may be a side by side arrangement or an "islands-in-the-sea" arrangement. Conjugate fibers are taught in U.S. Pat. No. 5,108,820 to Kaneko et al., U.S. Pat. No. 5,336,552 to Strack et al., and U.S. Pat. No. 5,382,400 to Pike et al. For two component fibers, the polymers may be present in ratios of 75/25, 50/50, 25/75 or any other desired ratios.

As used herein the term "biconstituent fibers" refers to fibers which have been formed from at least two polymers extruded from the same extruder as a blend. The term "blend" is defined below. Biconstituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random. Biconstituent fibers are sometimes also referred to as multiconstituent fibers. Fibers of this general type are discussed in, for example, U.S. Pat. No. 5,108,827 to Gessner. Bicomponent and biconstituent fibers are also discussed in the textbook *Polymer Blends and Composites* by John is A. Manson and Leslie H. Sperling, copyright 1976 by Plenum Press, a division of Plenum Publishing Corporation of New York, IBSN 0-306-30831-2, at pages 273 through 277.

As used herein the term "blend" as applied to polymers, means a mixture of two or more polymers while the term "alloy" means a sub-class of blends wherein the components are immiscible but have been compatibilized. "Miscibility" and "immiscibility" are defined as blends having negative and positive values, respectively, for the free energy of mixing. Further, "compatibilization" is defined as the process of modifying the interfacial properties of an immiscible polymer blend in order to make an alloy.

As used herein, through air bonding or "TAB" means a process of bonding a nonwoven, for example, a bicomponent fiber web in which air which is sufficiently hot to melt one of the polymers of which the fibers of the web are made is forced through the web. The air velocity is often between 100 and 500 feet per minute and the dwell time may be as long as 6 seconds. The melting and resolidification of the polymer provide the bonding. Through air bonding has restricted variability and is often regarded a second step bonding process. Since TAB requires the melting of at least one component to accomplish bonding, it is restricted to webs with two components such as bicomponent fiber webs or webs containing an adhesive fiber, powder or the like. TAB is frequently used to bond BCW materials.

As used herein "thermal point bonding" involves passing a fabric or web of fibers to be bonded between a heated calender roll and an anvil roll. The calender roll is usually, though not always, patterned in some way so that the entire fabric is not bonded across its entire surface. As a result, various patterns for calender rolls have been developed for functional as well as aesthetic reasons. One example of a pattern has points and is the Hansen Pennings or "H&P" pattern with about a 30% bond area with about 200 bonds/square inch as taught in U.S. Pat. No. 3,855,046 to Hansen and Pennings. The H&P pattern has square point or pin bonding areas wherein each pin has a side dimension of 0.038 inches (0.965 mm), a spacing of 0.070 inches (1.778 mm) between pins, and a depth of bonding of 0.023 inches (0.584 mm). The resulting pattern has a bonded area of about 29.5%. Another typical point bonding pattern is the expanded Hansen and Pennings or "EHP" bond pattern which produces a 15% bond area with a square pin having a side dimension of 0.037 inches (0.94 mm), a pin spacing of 0.097 inches (2.464 mm) and a depth of 0.039 inches (0.991 mm). Another typical point bonding pattern designated "714" has square pin bonding areas wherein each pin has a side dimension of 0.023 inches, a spacing of 0.062 inches (1.575 mm) between pins, and a depth of bonding of 0.033 inches (0.838 mm). The resulting pattern has a bonded area of about 15%. Yet another common pattern is the C-Star pattern which has a bond area of about 16.9%. The C-Star pattern has a cross-directional bar or "corduroy" design interrupted by shooting stars. Other common patterns include a diamond pattern with repeating and slightly offset diamonds and a wire weave pattern looking as the name suggests, e.g. like a window screen. Typically, the percent bonding area varies from around 10% to around 30% of the area of the fabric laminate web. As in well known in the art, the spot bonding holds the laminate layers together as well as imparts integrity to each individual layer by bonding filaments and/or fibers within each layer.

As used herein, the term "personal care product" means diapers, training pants, absorbent underpants, adult incontinence products, sanitary wipes and feminine hygiene products such as sanitary napkins and tampons.

As used herein, the term "hydrophilic" means that the polymeric material has a surface free energy such that the polymeric material is wettable by an aqueous medium, i.e. a liquid medium of which water is a major component. The term "hydrophobic" includes those materials that are not hydrophilic as defined. The phrase "naturally hydrophobic"refers to those materials that are hydrophobic in their chemical composition state without additives or treatments affecting the hydrophobicity. It will be recognized that hydrophobic materials may be treated internally or externally with surfactants and the like to render them hydrophilic.

It is also possible to have other materials blended with the polymer used to produce a nonwoven according to this invention such as pigments to give each layer the same or distinct colors. Pigments for spunbond and meltblown thermoplastic polymers are known in the art and are internal additives. A pigment, if used, is generally present in an amount less than about 5 weight percent of the layer while other additives may be present in a cumulative amount less than about 25 weight percent.

The fibers from which the fabric of this invention is made may be produced, for example, by the meltblowing or spunbonding processes, including those producing bicomponent, biconstituent or polymer blend fibers which are well known in the art. These processes generally use an extruder to supply melted thermoplastic polymer to a spinneret where the polymer is fiberized to yield fibers which may be staple length or longer. The fibers are then drawn, usually pneumatically, and deposited on a moving formations mat or belt to form the nonwoven fabric. The fibers produced in the spunbond and meltblown processes are microfibers as defined above.

The manufacture of meltblown webs is discussed generally above and in the references.

As mentioned, the nonwoven also may be a bonded carded web. Bonded carded webs are made from staple fibers, which are usually purchased in bales. The bales are placed in a picker, which separates the fibers. Then, the fibers are sent through a combing or carding unit, which further breaks apart and aligns the staple fibers in the machine direction to form a generally machine direction-oriented fibrous nonwoven web. Once the web is formed, it then is bonded by one or more of several known bonding methods. One such bonding method is powder bonding, wherein a powdered adhesive is distributed through the web and then activated, usually by heating the web and adhesive with hot air. Another suitable bonding method is pattern bonding, wherein heated calender rolls or ultrasonic bonding equipment are used to bond the fibers together, usually in a localized bond pattern, though the web can be bonded across its entire surface if so desired. Another suitable bonding method, particularly when using bicomponent staple fibers, is through-air bonding.

The fabric used in this invention may be a multilayer laminate. An example of multilayer laminate is an embodiment wherein some of the layers are spunbond and some meltblown such as a spunbond/meltblown/spunbond (SMS) laminate as disclosed in U.S. Pat. No. 4,041,203 to Brock et al., U.S. Pat. No. 5,169,706 to Collier, et al, and U.S. Pat. No. 4,374,888 to Bornslaeger. Such a laminate may be made by sequentially depositing onto a moving forming belt first a spunbond fabric layer, then a meltblown fabric layer and last another spunbond layer and then bonding the laminate in a manner described below. Alternatively, the fabric layers may be made individually, collected in rolls, and combined in a separate bonding step. Such fabrics usually have a basis weight of from about 0.1 to 12 osy (6 to 400 gsm), or more particularly from about 0.75 to about 3 osy. The treatment in accordance with the invention may be carried out inline with the nonwoven manufacturing process or offline on previously produced substrates or nonwovens.

Spunbond nonwoven fabrics are generally bonded in some manner as they are produced in order to give them sufficient structural integrity to withstand the rigors of further processing into a finished product. Bonding can be accomplished in a number of ways such as hydroentanglement, needling, ultrasonic bonding, adhesive bonding, stitchbonding, through-air bonding and thermal bonding.

For some applications it may be desired to apply a corona treatment to the web or otherwise expose it to a reactive species prior to applying the viscoelastant. Such treatments are described in coassigned U.S. Pat. No. 5,814,567 to Yahiaoui, Ning, Bolian, McDowall, Potts and Van Hout filed Jun. 14, 1996, incorporated herein in its entirety by reference.

The field of reactive species serves to increase the affinity of the hydrophilic polymeric material for the porous hydrophobic polymer substrate. The field of reactive species may be, by way of example, a corona field. As another example, the field of reactive species may be a plasma field.

Without wishing to be bound by theory, it is believed that exposure of the porous hydrophobic polymer substrate to a field of reactive species results in alterations of the surfaces of the substrate, thereby temporarily raising the surface energy of the substrate. This, in turn, allows the penetration of the treating solution into the porous substrate; that is, the porous substrate may be saturated with the treating solution.

Although exposure of the porous substrate to a field of reactive species is a desired method of temporarily raising the surface energy of the substrate, other procedures may be employed. For example, the porous substrate may be treated with ozone or passed through an oxidizing solution, such as an aqueous medium containing chromium trioxide and sulfuric acid. Care should be taken with such other procedures, however, to either prevent or minimize degradation of the porous substrate.

The strength of the field of reactive species may be varied in a controlled manner across at least one dimension of the fibrous web. Upon coating the porous substrate with the hydrophilic polymeric material, the extent or degree of hydrophilicity of the coating is directly proportional to the strength of the field. Thus, the hydrophilicity of the coating of polymeric material will vary in a controlled manner across at least one dimension of the fibrous web.

The strength of the field of reactive species is readily varied in a controlled manner by known means. For example, a corona apparatus having a segmented electrode may be employed, in which the distance of each segment from the sample to be treated may be varied independently. As another example, a corona apparatus having a gap-gradient electrode system may be utilized; in this case, one electrode may be rotated about an axis which is normal to the length of the electrode. Other methods also may be employed; see, for example, "Fabrication of a Continuous Wettability Gradient by Radio Frequency Plasma Discharge," W. G. Pitt, *J. Colloid Interface Sci.*, 133, No. 1, 223 (1989); and "Wettability Gradient Surfaces Prepared by Corona Discharge Treatment," J. H. Lee, et al., *Transactions of the 17th Annual Meeting of the Society for Biomaterials*, May, 1991, 1–5, page 133, Scottsdale, Ariz.

As alluded to above, an important parameter for treated nonwovens for many applications involving viscoelastic fluids such as distribution layers for sanitary napkins is wicking or the ability to rapidly distribute menses in use so as to take maximum advantage of the absorbency of the product.

Prior surfactant treatments such as ethoxylated hydrocarbons, siloxanes, and ionic surfactants have been shown to aid wicking, but not via the mechanism of the present invention. Such conventional surfactants increase wettability but fail to effectively reduce the viscoelasticity of menses in a manner to enhance wicking to the degree of the present invention. In accordance with the invention, it has been found that use of viscoelastants such as specific alkyl polyglycosides not only reduces the viscoelastic properties of the insult fluid but also provides surfactant properties to rapidly distribute the viscoelastic fluid. For best results the alkyl polyglycoside is one with 8–10 carbons in the alkyl chain and is included in an amount of about 0.2% to about 5% based on the total material weight and the weight of the alkyl polyglycoside composition, which may be aqueous, containing about 40% water, for example. Other viscoelastants will be apparent to those skilled in this art and include, for example, bovine lipid extract surfactant (Survanta®, Ross Laboratories) and protein-cleaving enzymes such as papain and pepsin as well as certain dextrins and dextrans.

Table 1 below illustrates the effects on the Theological properties of an eggwhite-based viscoelastic fluid (described above under TEST METHODS as "Fluid A") of the addition of a viscoelastant, Glucopon 220UP, obtained as a 60% (by weight) solution of alkyl polyglycoside in water, available from Henkel Corporation. Rheological measurements were made on the egg-white based viscoelastic fluid (Fluid A) with and without the addition of Glucopon 220. Glucopon was added to the viscoelastic fluid by direct addition and mixed intermittently for at least 24 hours to insure complete mixing. The final concentration of Glucopon 220 mixed into the viscoelastic fluid was 1.0%. The viscoelastic fluid without Glucopon 220 was also mixed intermittently for at least 24 hours to duplicate the same shear history as the Glucopon containing fluid. The measurements were made as described in the Test Method section. The elastic stress at a strain of approximately 1 was reduced by 36% while the viscosity at a shear rate of approximately 0.1 sec$^{-1}$ was reduced by 30%. Percentages were obtained using the difference between Control and Viscoelastant divided by Control and multiplying the result by 100.

TABLE 1

Properties

| Sample | Elastic Stress (dyne/cm$^2$) | Viscosity (poise) |
|---|---|---|
| Control | 0.0848 | 0.423 |
| Viscoelastant | 0.0540 | 0.296 |
| Conditions | ~1 (Strain) | ~0.1 sec$^{-1}$ (Strain rate) |

Figure 3:
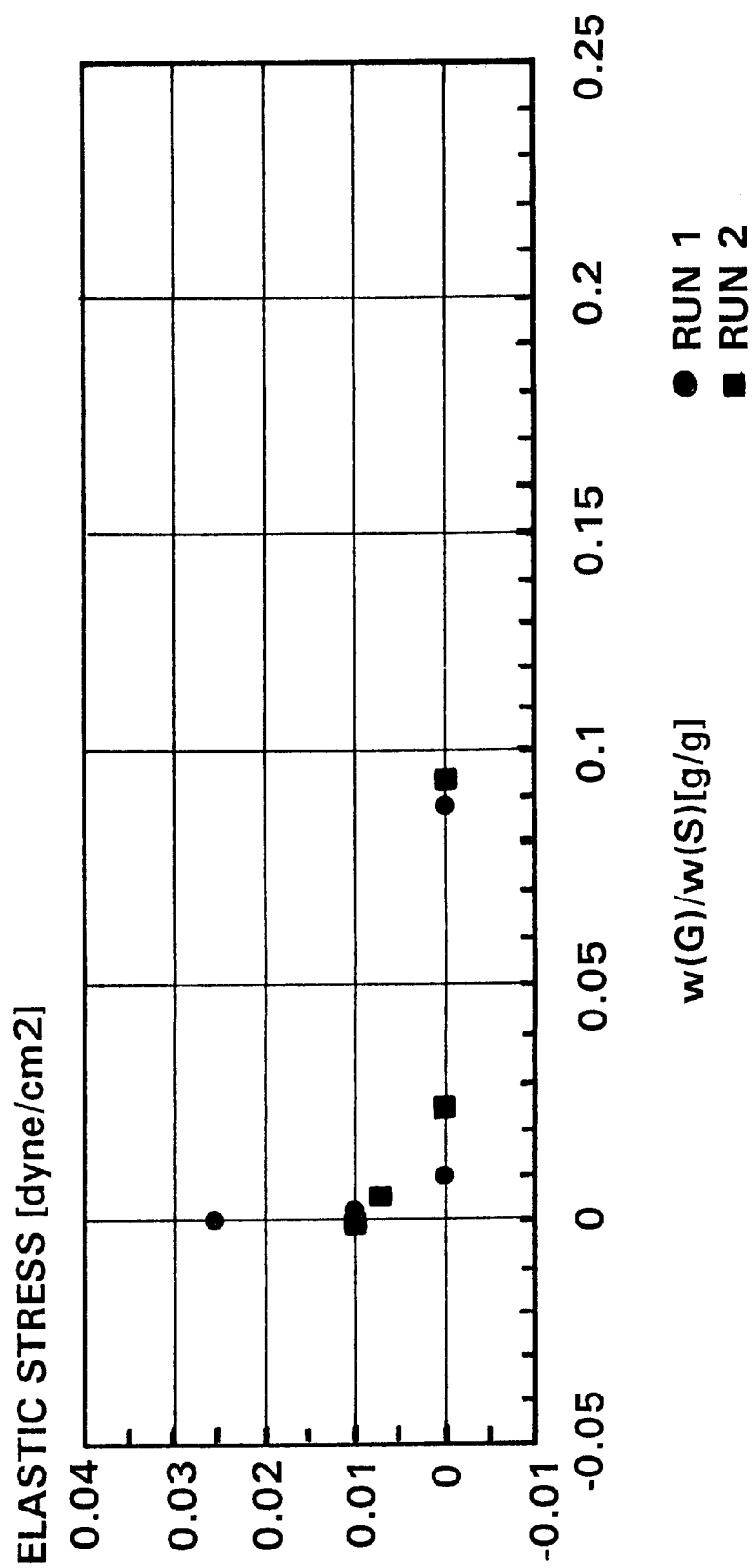
FIG. 3 is a graph of elastic stress measurements of a viscoelastic composition as a function of viscoelastant addition.
Figure 4:
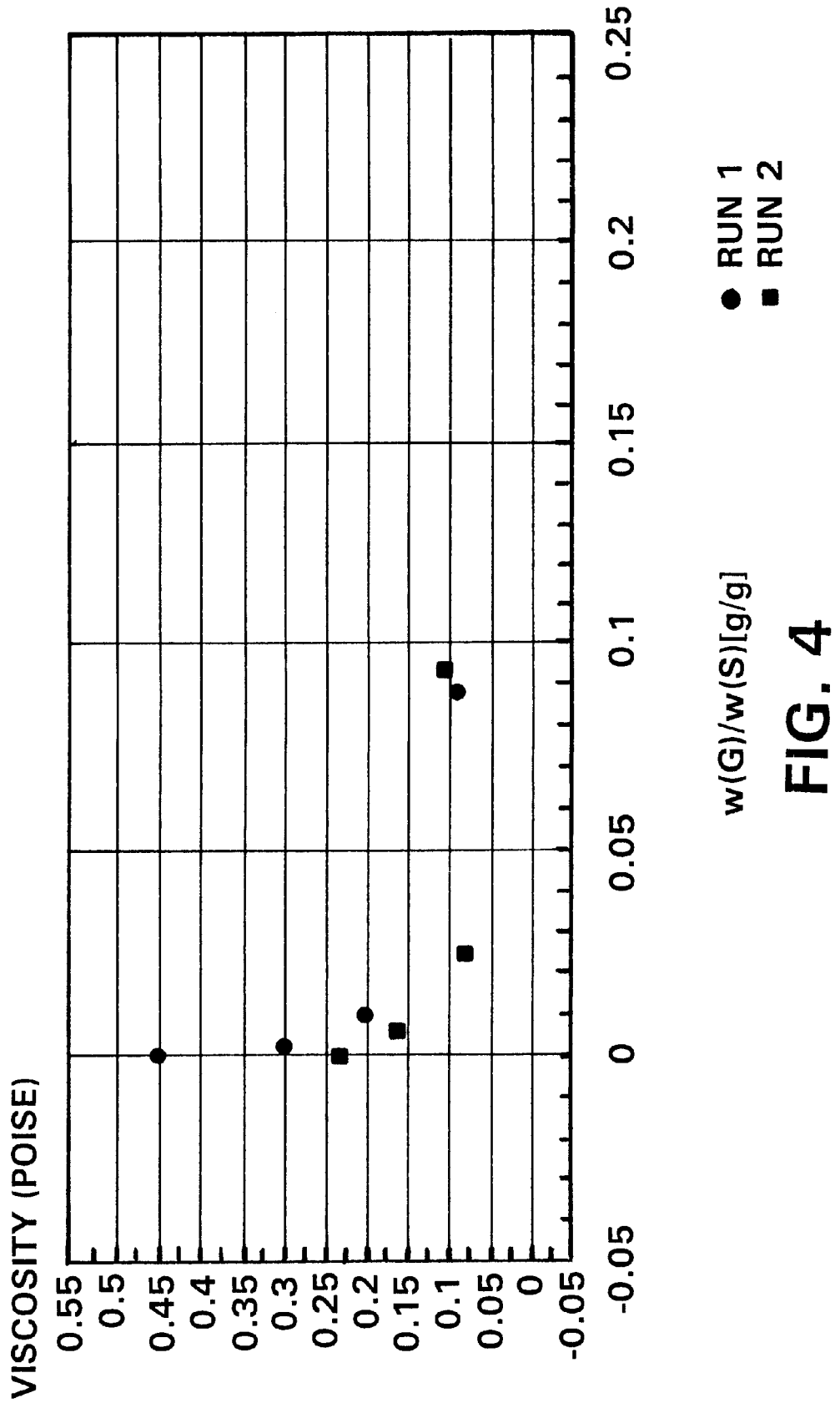
FIG. 4 is a graph of viscosity measurements of a viscoelastic composition as a function of viscoelastant addition.

Table 2 and FIGS. 3 and 4 show the results of a similar example (Run 1 of FIGS. 3 and 4) using a second viscoelastic fluid (Fluid B). For this example the viscoelastant and viscoelastic fluid were mixed either by inversion 10 times and standing for 1 hour or using a stirring rod for 1 minute and standing for at least 30 minutes. The preparation differences are believed to have only slightly affected test results, if at all. In this case the amount of Glucopon 220 viscoelastant mixed into the viscoelastic fluid was at least about 1.0%. The elastic stress at a strain of about 1 was reduced within the range of 60 to 100% (considering the sensitivity limitations of the equipment) while the viscosity at a shear rate of about 0.1 sec$^{-1}$ was reduced by about 77% indicating that the invention is applicable to different viscoelastic fluids.

TABLE 2

Properties

| Sample | Elastic Stress (dyne/cm$^2$) | Viscosity (poise) |
|---|---|---|
| Control | 0.3 | 0.09 |
| Viscoelastant | 0.106 | 0.1 |
| Test condition: | Strain = 1 | Strain rate = 0.1 Sec$^{-1}$ |

FIGS. 3 and 4 illustrate these results as a function of amount of viscoelastant added. As clearly shown, the amount of viscoelastant has a dramatic effect reducing both elastic stress and viscosity of the viscoelastic fluid (Fluid B).

The present invention is believed applicable to reduced viscoelasticity treatment and improved fluid handling with a variety of viscoelastic fluid compositions, although the sanitary napkin application represents a very desirable use.

Table 3 below shows wicking results in a bonded carded web of the type that might be used as a distribution layer in a sanitary napkin construction. The bonded carded web constructed for purposes of these tests was a through-air bonded carded web, or TABCW, prepared as described below. Washed fabrics, or the identical fabrics prepared with four different surface treatments, were tested. Wicking studies were conducted with an eggwhite-based viscoelastic fluid (described above in TEST METHODS Fluid A); distance wicked horizontally during a 20 minute exposure of the fabric to the fluid was measured. Glucopon-treated TABCW fabrics demonstrated the greatest wicking distances.

TABLE 3

| SAMPLE | WICKING (in) AVG | STD DEV |
|---|---|---|
| MATERIAL A | 3.27 | 0.29 |
| MATERIAL B | 1.63 | 0.19 |
| MATERIAL C | 2.35 | 0.45 |
| MATERIAL D | 0.53 | 0.22 |

The web was composed of 100% by weight 3.0 denier polyethylene sheath/polypropylene core bicomponent staple fibers having a length of 38 millimeters. The bicomponent fibers were obtained from Chisso Corporation and were supplied with a vendor fiber finish. The staple fibers were all sent through an opener and were uniformly mixed together before being carded into a web at a line speed of 15.24 meters per minute (50 feet per minute). Once the web was formed, it was sent through a through-air bonder (drum type) with an air temperature of 131° C. The dwell time within the bonder was between 3 and 4.5 seconds. The resultant web had a basis weight of 100 gsm and a density of 0.06 gm/cm$^3$. The web was then wound up on a roll.

Material A is the above described web which was washed to remove the vendor fiber finish and then treated with 2.0% Glucopon 220 as described below. Material B is the above described web which was washed to remove the vendor fiber finish and then treated with 0.45% calcium alginate as described below. Material C is the above described web with the vendor fiber finish. Material D is the above described web with which was washed to remove the vendor fiber finish.

Figure 5:
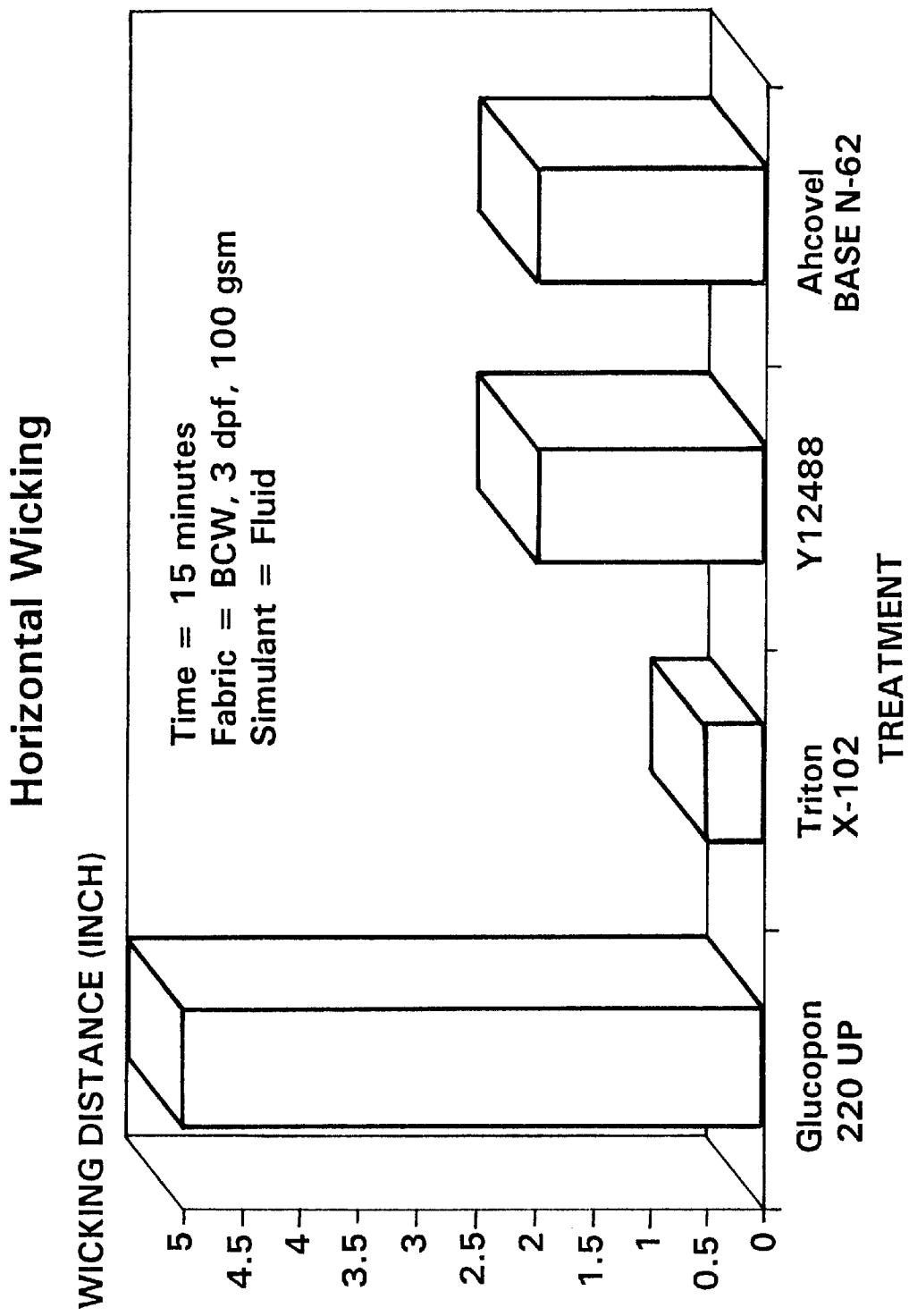
FIG. 5 is a graph comparing wicking distance tests on material in accordance with the invention with other treatments.

FIG. 5 presents wicking distance comparisons with several other known nonwoven web treatments. The base web was as described as Material A above, and the viscoelastic fluid was menses simulant (Fluid B). Triton X-102 is an alkylphenol ethoxylate surfactant available from Union Carbide. Y12488 is an ethoxylated polydimethyl siloxane available from Osi. Ahcovel N-62 is a blend of ethoxylated hydrogenated castor oil and sorbitan monooleate available from ICI. The amount of each applied to the web by weight was 0.6% viscoelastant (based on active ingredients), 0.5% by weight, Triton 102, 1% by weight Y12488, and 1.5% by weight Ahcovel. As shown, the results measured after 15 minutes show that viscoelastants used in accordance with the invention increase wicking distance substantially.

In order to demonstrate effectiveness of other viscoelastants such as dextran (4000 MW oligosaccharide available from Polydex Pharmaceuticals, Ltd. Of Scarborough, Toronto, Canada), a BCW sample of Chisso bicomponent fibers as described above was oxidized in a Branson/IPC Model PM 119 plasma treater at 100 watts of power in an air plasma at 0.6 torr for 5 minutes. The fabric rendered wettable by the plasma was then immediately immersed in an aqueous solution of the treating substance. Table 4 gives the concentration of the treating substances.

TABLE 4

| Substance Being Tested | Concentration (wt./vol.) |
|---|---|
| Dextran (4,000 MW) | 3% |
| Dextran (4,000 MW) | 0.6% |
| Sodium Alginate | 1% |
| Maltose | 3% |

Excess solution was removed from the saturated fabric by vacuum extraction (passing the saturated fabric over a slot that a vacuum was applied to). After vacuum extraction the fabrics measured about 100% wet pickup of the treating solution by weight. The treated fabrics were dried at 80 degrees C. for 8 hours or until constant weight and then tested for wicking.

The surfactants to be tested were treated as above except the oxidation step was omitted. The solution concentrations were as described in Table 5.

TABLE 5

| Substance Being Tested | Concentration (wt./vol.) |
|---|---|
| Glucopon 600 (alkyl polyglycoside with 12–18 carbons in alkyl chain from Henkel) | 3% |
| Triton X-102 | 2% |
| Glucopon 220 (an alkyl polyglycoside with 8–12 carbons in alkyl chain available from Henkel) | 2% |

Figure 6:
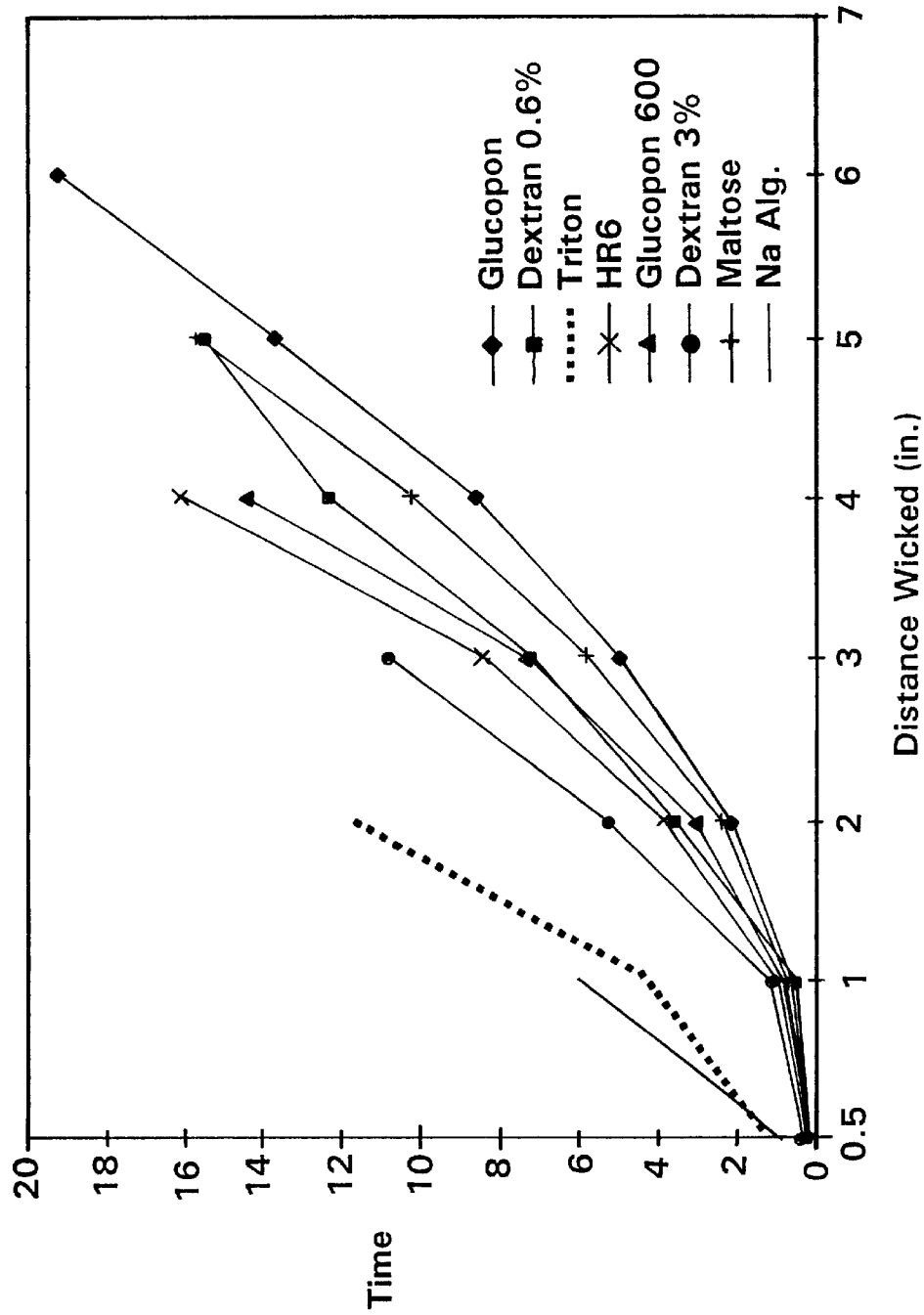
FIG. 6 is a graph showing additional wicking distance comparisons.

FIG. 6 shows the results of wicking tests using Fluid B with regard to these materials as well as Material C ("HR6"). As shown surfactants alone such as sodium alginate and Triton X-102 have reduced wicking benefit. Use of viscoelastants in accordance with the invention, however, provide a wide range of wicking improvement allowing this property to be tailored to a particular use.

Table 6 shows that selection of a particular viscoelastant can be made to have a predominant effect on either the viscosity or the elasticity of the viscoelastic fluid. Tests were run on Fluid B samples after mixing 1 gram of test solution (0.9% saline solution in the case of the Control) with 9 grams of simulant by slow inversion for 15 minutes. As shown Glucopon 220 dramatically affects both viscosity and elasticity whereas Dextran affects elasticity to a greater degree than it does viscosity.

TABLE 6

|  | Simulant (Control) | 1% Glucopon in Simulant | 1% Dextran in Simulant |
|---|---|---|---|
| Viscosity (Poise) Measured at a shear rate of 0.1/Sec. | 0.461 | 0.110 | 0.390 |
| Elasticity (Poise) Measured at a shear rate of 0.01/Sec. | 0.566 | ~0 | 0.275 |

Material A was prepared by cutting the web into a sample 10 inches (about 25 cm) by 12 inches (about 30 cm). The sample was gently rinsed in 100° F. tap water for 5 minutes followed by deionized water for one minute to remove essentially all of the vendor fiber finish and dried overnight in an air-circulating oven at 35° C. The sample was then immersed for about 5 seconds in a solution consisting of 200 g of Glucopon 220UP (Henkel Corporation) as supplied, which is 60% active in water, and 30 g hexanol (Catalog No. H1,330-3, Aldrich Chemical Company, Milwaukee, Wiss.) in 6000 g deionized water at ambient temperature (20–25° C.). The solution contained 2.0 percent by weight of active Glucopon 220UP. Excess solution was removed from the wetted fabric by vacuum extraction (i.e. passing the wetted fabric over a slot to which vacuum was applied). The sample contained approximately 100 percent by weight wet pickup based on the dry weight of the sample of the solution after vacuum extraction. The sample was then dried over night in an oven at 35° C. The hexanol was completely eliminated during drying.

Material B was prepared by a plasma method similar to that disclosed in coassigned U.S. Pat. No. 5,814,567 filed Jun. 14, 1996, discussed above. The web was washed and dried to remove the vendor finish as described for Material A. The sample was oxidized in a Branson/IPC Model PM119 plasma treater at 80 watts of power in an air plasma at 0.6 torr for 4 minutes. The sample then was immersed for about 30 seconds in a solution consisting of 23.8 g of calcium chloride dihydrate (Catalog No. 22,350-6, Aldrich Chemical Company, Milwaukee, Wiss.) and 6000 g of deionized water. The solution contained 0.3 percent of weight of calcium chloride. Excess solution was removed from the wetted fabric by vacuum extraction (i.e. passing the wetted fabric over a slot to which a vacuum was applied). The sample contained approximately 150 percent by weight wet pickup (based on the dry weight of the sample) of the calcium chloride solution after vacuum extraction. The still wet sample was dipped for about 30 seconds in a solution composed of 18.0 g or 0.3 percent by weight of high viscosity sodium alginate (Catalog No. A-7128, Sigma Chemical Company, St. Louis, Mo.) in 6,000 g deionized water for about 30 seconds. Excess solution was removed from the wet sample by vacuum extraction. The sample contained a total of approximately 300 percent of both the calcium chloride and sodium alginate solutions, resulting in the formation of a calcium alginate gel on the fibers of the sample. The sample then was dried overnight in an oven at 35° C.

Material D was prepared by washing the web to remove essentially all of the vendor finish and drying as described for Materials A and B.

The viscoelastant such as an alkyl polyglycoside treating composition may contain other additives as appropriate for the desired result so long as they do not have a major detrimental effect on the activity of the modifier such as the alkyl polyglycoside. Examples of such additives include additional conventional surfactants such as ethoxylated hydrocarbons or ionic surfactants, or co-wetting aids such as low molecular weight alcohols. As mentioned, the composition is desirably applied from high solids, advantageously 80% or less solvent or water, so as to minimize drying and its attendant costs and deleterious effects. The treating composition may be applied in varying amounts depending on the desired results and application. For sanitary napkin distribution layer applications, for example, effective results are obtained within a range of about 0.1% to about 5.0% solids add-on based on the dry weight of the fabric, with a range of about 0.2% to 3.0% being advantageous from the perspective of both cost and performance. Also, as will be recognized by those skilled in this art, many substrate materials may be treated in accordance with the invention including nonwovens such as spunbond, meltblown, carded webs and others as well as woven webs and even films and the like where improved fluid distribution is desired. It will also be recognized by those skilled in this art that some viscoelastants may be used as internal additives, that is, added to the polymer melt directly or in a concentrate form. After fiber formation, such additives will migrate to the fiber surface and impart the desired effect. For further discussion of internal addition of additives, reference may be had to coassigned U.S. Pat. No. 5,540,979 to Yahiaoui, Potts, Perkins, Powers and Jascomb issued Jul. 20, 1996, the contents of which are incorporated entirely herein by reference. The substrate basis weight is not critical and may vary widely depending on the application. For sanitary napkin distribution layer applications, spunbond and bonded carded webs are often used with basis weights generally in the range of from about 7 gsm to about 175 gsm.

Examples of the alkyl polyglycoside viscoelastants include Glucopon 225 or 220, both alkyl polyglycosides with 8–10 carbon atoms in the alkyl chain and available from Henkel Corporation as well as Crodesta SL-40 (sucrose cocoate) from Creda, TL 2141 (Glucopon 220 analog) from ICI.

Referring to FIG. 1, a process will be described for application to one or both sides of a traveling web. It will be appreciated by those skilled in the art that the invention is equally applicable to inline treatment or a separate, offline treatment step. Web 12, for example a spunbond or meltblown nonwoven is directed over support rolls 15, to a treating station including rotary spray heads 22 for application to one side 14 of web 12. An optional treating station (shown in phantom) which may include rotary spray heads 18 can also be used to apply to opposite side 23 of web 12 traveling over support rolls 17,19. Each treatment station receives a supply of treating liquid 30 from a reservoir (not shown). The treated web may then be dried if needed by passing over dryer cans 25 or other drying means and then wound as a roll or converted to the use for which it is intended. Alternative drying means include ovens, through air dryers, infra red dryers, air blowers, and the like.

Figure 2:
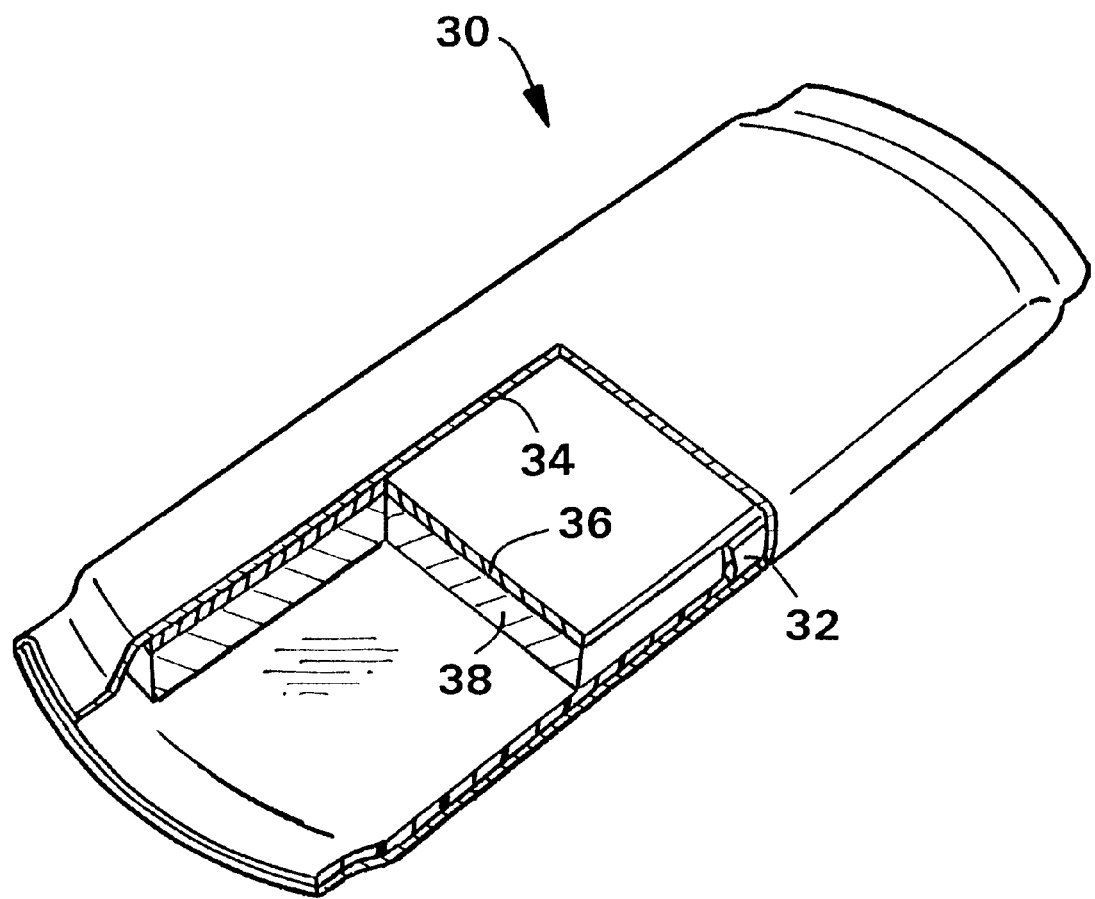
FIG. 2 is a representative personal care product in the form of a sanitary napkin incorporating a cover of a treated fabric in accordance with the present invention.

FIG. 2 illustrates a representative personal care product in the form of a sanitary napkin structure incorporating a distribution layer in accordance with the present invention. As shown, sanitary napkin 30 includes impervious backing 40, absorbent 38, distribution layer 36, and cover or body contacting layer 34. If desired, the absorbent 38 may also be enclosed on its bottom and sides by wrap 32 for enhanced protection against side leakage. In accordance with the invention, either or all of the cover, distribution or absorbent layers may be treated with a viscoelastant.

Thus, in accordance with the invention, there has been provided an improved treatment process and resulting treated nonwovens and products incorporating them that provide the benefits described above. While the invention has been illustrated by specific embodiments, it is not limited thereto and is intended to cover all equivalents as come within the broad scope of the claims.

We claim:

1. A structure adapted to receive a fluid having viscoelastic properties, said structure comprising a synthetic substrate containing a viscoelastant on the surface thereof so as to be contacted by said viscoelastic fluid and thereby materially affect the viscoelastic properties of the viscoelastic fluid.

2. The structure of claim 1 wherein said synthetic substrate comprises a film.

3. The structure of claim 1 wherein said synthetic substrate is a naturally hydrophobic nonwoven.

4. The structure of claim 3 wherein said viscoelastant comprises an oligosaccharide.

5. The structure of claim 2 wherein said nonwoven comprises a propylene polymer spunbond.

6. The structure of claim 3 wherein said viscoelastant is an alkyl polyglycoside having 8 to 10 carbon atoms in the alkyl chain.

7. The structure of claim 6 wherein said nonwoven fabric comprises a spunbond nonwoven.

8. The structure of claim 6 wherein said viscoelastant is present in an amount of from about 0.1 to about 5.0% solids add on based on the dry weight of the nonwoven web.

9. A personal care product comprising an impervious backing, an absorbent, and a body contact layer, wherein said body contact layer comprises the structure of claim 8.

10. The personal care product of claim 9 as a menses absorbent device.

11. The menses absorbent device of claim 10 in the form of a sanitary napkin werein said structure comprises a sanitary napkin distribution layer.

12. The personal care product of claim 9 as a feces containment device.

13. The personal care product of claim 12 as a disposable diaper wherein said structure comprises a diaper liner.

14. The personal care product of claim 12 as an incontinent care product.

15. The structure of claim 6 wherein said nonwoven comprises a propylene polymer spunbond.

16. A personal care product comprising an impervious backing, an absorbent, and a body contact layer, wherein said body contact layer comprises the structure of claim 6.

17. The personal care product of claim 16 as a feces containment device.

18. The personal care product of claim 17 as a disposable diaper wherein said structure comprises a diaper liner.

19. The personal care product of claim 17 as an incontinent care product.

20. The personal care product of claim 16 as a menses absorbent device.

21. The menses absorbent device of claim 20 in the form of a sanitary napkin wherein said structure comprises a sanitary napkin distribution layer.

22. A sanitary napkin comprising a cover, a backing and an absorbent located between said cover and said backing wherein a distribution layer containing an effective amount of a viscoelastant is located between said cover and said absorbent in a position to be contacted by menses in use.

23. A process for absorbing a viscoelastic fluid comprising the step of contacting said viscoelastic fluid with a substrate containing an effective amount of a viscoelastant.

* * * * *